(12) United States Patent
Boualleg et al.

(10) Patent No.: US 10,618,033 B2
(45) Date of Patent: Apr. 14, 2020

(54) MESOPOROUS AND MACROPOROUS NICKEL-BASED CATALYST HAVING A MEDIAN MACROPORE DIAMETER OF GREATER THAN 200 NM AND ITS USE WITH REGARD TO HYDROGENATION

(71) Applicant: IFP Energies nouvelles, Rueil-Malmaison (FR)

(72) Inventors: Malika Boualleg, Villeurbanne (FR); Anne-Claire Dubreuil, Lyons (FR); Emily Maille, Lyons (FR); Cecile Thomazeau, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 22 days.

(21) Appl. No.: 15/318,615

(22) PCT Filed: Jun. 9, 2015

(86) PCT No.: PCT/EP2015/062815
§ 371 (c)(1),
(2) Date: Dec. 13, 2016

(87) PCT Pub. No.: WO2015/189189
PCT Pub. Date: Dec. 17, 2015

(65) Prior Publication Data
US 2017/0128912 A1 May 11, 2017

(30) Foreign Application Priority Data
Jun. 13, 2014 (FR) ...................... 14 55434

(51) Int. Cl.
| | | |
|---|---|---|
| *B01J 21/04* | (2006.01) | |
| *B01J 23/755* | (2006.01) | |
| *B01J 35/02* | (2006.01) | |
| *B01J 35/10* | (2006.01) | |
| *B01J 37/00* | (2006.01) | |
| *B01J 37/02* | (2006.01) | |
| *B01J 37/03* | (2006.01) | |
| *B01J 37/08* | (2006.01) | |
| *B01J 37/16* | (2006.01) | |
| *C07C 5/03* | (2006.01) | |
| *C07C 5/10* | (2006.01) | |
| *C10G 45/48* | (2006.01) | |

(Continued)

(52) U.S. Cl.
CPC ............ *B01J 21/04* (2013.01); *B01J 23/755* (2013.01); *B01J 23/835* (2013.01); *B01J 23/892* (2013.01); *B01J 27/1853* (2013.01); *B01J 35/023* (2013.01); *B01J 35/108* (2013.01); *B01J 35/109* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 37/0009* (2013.01); *B01J 37/009* (2013.01); *B01J 37/0201* (2013.01); *B01J 37/0207* (2013.01); *B01J 37/0236* (2013.01); *B01J 37/03* (2013.01); *B01J 37/031* (2013.01); *B01J 37/036* (2013.01); *B01J 37/08* (2013.01); *B01J 37/16* (2013.01); *B01J 37/18* (2013.01); *C07C 5/03* (2013.01); *C07C 5/05* (2013.01); *C07C 5/10* (2013.01); *C10G 45/36* (2013.01); *C10G 45/48* (2013.01); *B01J 33/00* (2013.01); *B01J 35/006* (2013.01); *B01J 35/026* (2013.01); *B01J 37/0045* (2013.01); *B01J 37/20* (2013.01); *C07C 2521/04* (2013.01); *C07C 2523/755* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 4,301,037 A | * | 11/1981 | Sanchez ................ B01J 21/04 264/142 |
| 4,631,265 A | | 12/1986 | Oudejans et al. |

(Continued)

FOREIGN PATENT DOCUMENTS

| | | |
|---|---|---|
| EP | 0168091 A1 | 1/1986 |
| EP | 0885844 A1 | 12/1998 |
| WO | 2005028106 A1 | 3/2005 |

OTHER PUBLICATIONS

International Search Report corresponding to PCT/EP2015/062815 date of completion Aug. 12, 2015; dated Sep. 9, 2015.

*Primary Examiner* — Colin W. Slifka
(74) *Attorney, Agent, or Firm* — Millen, White, Zelano & Branigan, PC; Ryan Pool

(57) ABSTRACT

The invention relates to a supported catalyst that comprises an oxide substrate that is for the most part calcined aluminum and an active phase that comprises nickel, with the nickel content being between 5 and 65% by weight of said element in relation to the total mass of the catalyst, with said active phase not comprising a metal from group VIB, the nickel particles having a diameter that is less than or equal to 20 nm, said catalyst having a median mesopore diameter of between 8 nm and 25 nm, a median macropore diameter of greater than 200 nm, a mesopore volume that is measured by mercury porosimetry that is greater than or equal to 0.30 mL/g, and a total pore volume that is measured by mercury porosimetry that is greater than or equal to 0.34 mL/g. The invention also relates to the method for preparation of said catalyst and its use in a hydrogenation method.

12 Claims, No Drawings

(51) Int. Cl.
*B01J 23/835* (2006.01)
*B01J 23/89* (2006.01)
*C10G 45/36* (2006.01)
*B01J 27/185* (2006.01)
*C07C 5/05* (2006.01)
*B01J 37/18* (2006.01)
*B01J 33/00* (2006.01)
*B01J 37/20* (2006.01)
*B01J 35/00* (2006.01)

(56) References Cited

U.S. PATENT DOCUMENTS

| | | |
|---|---|---|
| 4,657,889 A | 4/1987 | Ganguli et al. |
| 4,683,088 A | 7/1987 | Oudejans et al. |
| 4,734,392 A | 3/1988 | Ganguli et al. |
| 4,920,089 A * | 4/1990 | Van Beek ............... B01J 21/04 |
| | | 208/143 |
| 5,047,178 A | 9/1991 | Ganguli et al. |
| 5,478,791 A | 12/1995 | Baldauf et al. |
| 6,171,573 B1 | 1/2001 | Sato |
| 6,589,908 B1 | 7/2003 | Ginestra et al. |
| 2003/0125198 A1 | 7/2003 | Ginestra et al. |
| 2005/0101480 A1 | 5/2005 | Ackerman et al. |
| 2010/0276339 A1 | 11/2010 | Ginestra et al. |

* cited by examiner

MESOPOROUS AND MACROPOROUS NICKEL-BASED CATALYST HAVING A MEDIAN MACROPORE DIAMETER OF GREATER THAN 200 NM AND ITS USE WITH REGARD TO HYDROGENATION

FIELD OF THE INVENTION

The invention has as its object a catalyst that is supported on an oxide substrate that is for the most part calcined aluminum with an active nickel phase having a texture and a formulation that are favorable to hydrogenation reactions, in particular to reactions for selective hydrogenation of polyunsaturated compounds or for hydrogenation of aromatic compounds. The invention also relates to the method for preparation of said catalyst as well as its use in hydrogenation reactions.

The catalysts for selective hydrogenation or for hydrogenation of aromatic compounds are generally based on metals from group VIII of the periodic table such as nickel. The metal comes in the form of nanometric metal particles that are deposited on a substrate that may be a refractory oxide. The metal content of the group VIII, the optional presence of a second metal element, the size of the metal particles, and the distribution of the active phase in the substrate as well as the nature and pore distribution of the substrate are parameters that have an importance relative to the performance values of catalysts.

The speed of the hydrogenation reaction is governed by multiple criteria, such as the diffusion of reagents on the surface of the catalyst (external diffusional limitations), the diffusion of reagents in the porosity of the substrate to the active sites (internal diffusional limitations), and the inherent properties of the active phase such as the size of metal particles and the distribution of the active phase within the substrate.

As regards the size of the metal particles, it is generally assumed that the catalyst is all the more active the smaller the size of the metal particles. In addition, it is important to obtain a size distribution of the particles centered on the optimal value as well as a narrow distribution around this value.

As regards internal diffusional limitations, it is important that the pore distribution of the macropores and mesopores be adapted to the desired reaction so as to ensure the diffusion of reagents in the porosity of the substrate to the active sites as well as the diffusion to the outside of the products that are formed. The importance of an adapted pore distribution and in particular the presence of macropores in a reaction for selective hydrogenation of a pyrolysis gasoline in the case of a palladium-based catalyst has been described by, for example, Z. Zhou, T. Zeng, Z. Cheng, W. Yuan, in AICHE Journal, 2011, Vol. 57, No. 8, pages 2198-2206.

Numerous developments thus relate to the optimization of the pore distribution of the catalyst by the optimization of the substrate of the catalyst.

The document WO2011/080515 describes a nickel-based hydrogenation catalyst on an alumina substrate that has a nickel content of more than 35% by weight, with said catalyst having a high dispersion of nickel (0) on the surface of an alumina with very open porosity and with a high specific surface area. The pore distribution of the substrate is bimodal: at least 30% of the total pore volume consists of pores that have a diameter of between 5 and 20 nm, and at least 20% of the total pore volume consists of pores that have a diameter of between 100 and 700 nm with a total pore volume of the substrate of at least 1.0 mL/g. The nickel surface area should be greater than or equal to 110 $m^2$ per gram of nickel.

In this context, one of the objectives of this invention is to propose a supported catalyst with an active nickel phase that has hydrogenation performance values in terms of activity that are at least as good as the known catalysts of the state of the art.

More particularly, the invention relates to a supported catalyst that comprises an oxide substrate that is for the most part calcined aluminum and an active phase that comprises nickel, with the nickel content being between 5 and 65% by weight of said element in relation to the total mass of the catalyst, with said active phase not comprising a metal from group VIB, the nickel particles having a diameter that is less than or equal to 20 nm, said catalyst having a median mesopore diameter of between 8 nm and 25 nm, a median macropore diameter of greater than 200 nm, a mesopore volume that is measured by mercury porosimetry that is greater than or equal to 0.30 mL/g, and a total pore volume that is measured by mercury porosimetry that is greater than or equal to 0.34 mL/g.

The applicant discovered that a catalyst that is prepared by impregnation of the active phase on an alumina that results from the calcination of a particular alumina gel that is prepared according to the preparation method described below makes it possible to obtain a catalyst that has a pore distribution as well as a nickel particle size that are particularly suited to hydrogenation reactions, in particular to reactions for selective hydrogenation of polyunsaturated molecules such as diolefins, acetylenic compounds or alkenylaromatic compounds, or to reactions for hydrogenation of aromatic compounds.

Actually, the pore distribution resulting from the method for preparation of the calcined aluminum oxide substrate obtained from a specific alumina gel makes it possible to provide a porosity that is particularly suited to promoting the diffusion of reagents in the porous medium and then their reaction with the active phase. Without being linked to any theory, it seems that the particular textural properties of the catalyst according to the invention, in particular a bimodal porosity with the presence of macropores and mesopores of controlled size, make it possible to obtain a catalyst that has hydrogenation performance values in terms of activity that are at least as good as the known catalysts of the state of the art. The catalyst according to the invention is distinguished by a high mesopore volume that is coupled with a consequent macropore volume but where said volume is not too high, with a median macropore diameter that is relatively high. Actually, it is well known that although the presence of a macropore volume can reduce the internal diffusional limitations, at the same time it weakens the mechanical strength of the catalyst. It is therefore important to control the percentage of the macropore volume in relation to the total pore volume so as to obtain a catalyst that has the desired catalytic performance values and sufficient mechanical strength. In addition, the presence of a high total pore volume of the catalyst according to the invention makes it possible to impregnate a high content of active phase in a single pass.

According to a variant, the substrate, before introduction of the active phase, has a pore volume that is contained in the pores with a diameter of between 100 and 700 nm that is less than 20% of the total pore volume of the substrate, preferably less than 15% of the total pore volume of the substrate.

According to a variant, the nickel content is between 10 and 34% by weight of said element in relation to the total mass of the catalyst.

According to a variant, the macropore volume of the catalyst is between 10 and 40% of the total pore volume.

According to a variant, the mesopore volume of the catalyst is between 0.35 mL/g and 0.8 mL/g.

According to a variant, the catalyst does not contain micropores.

The invention also relates to the method for preparation of said catalyst. The invention also relates to the use of the catalyst in a hydrogenation method in which the catalyst according to the invention, or that which can be prepared according to the preparation method according to the invention, is brought into contact in the presence of hydrogen with a hydrocarbon feedstock that contains polyunsaturated molecules and/or aromatic compounds in such a way as to obtain an effluent that is at least partially hydrogenated.

DETAILED DESCRIPTION

The Catalyst According to the Invention

The catalyst according to the invention comes in the form of a supported catalyst that comprises an oxide substrate that for the most part is calcined aluminum and a nickel-comprising active phase. The characteristics of the alumina gel that have led to obtaining the alumina that for the most part is contained in said substrate, as well as the textural properties obtained with the active phase, impart its specific properties to the catalyst according to the invention.

More particularly, the invention relates to a supported catalyst that comprises an oxide substrate that is for the most part calcined aluminum and a nickel-comprising active phase, with the nickel content being between 5 and 65% by weight of said element in relation to the total mass of the catalyst, with said active phase not comprising a metal from group VIB, the nickel particles having a diameter that is less than or equal to 20 nm, said catalyst having a median mesopore diameter of between 8 nm and 25 nm, a median macropore diameter of greater than 200 nm, a mesopore volume measured by mercury porosimetry that is greater than or equal to 0.30 mL/g, and a total pore volume that is measured by mercury porosimetry that is greater than or equal to 0.34 mL/g.

The catalyst according to the invention and the substrate that is used for the preparation of the catalyst according to the invention have particular textural properties, in particular a specific pore distribution, where the macropore and mesopore volumes are measured by mercury intrusion, and the micropore volume is measured by nitrogen adsorption.

"Macropores" are defined as pores whose openings are greater than 50 nm and less than 7000 nm.

"Mesopores" are defined as pores whose openings are between 2 nm and 50 nm, inclusive.

"Micropores" are defined as pores whose openings are less than 2 nm.

Total pore volume of the catalyst or of the substrate used for the preparation of the catalyst according to the invention is defined as the volume that is measured by mercury intrusion porosimetry according to the Standard ASTM D4284-83 at a maximum pressure of 4000 bar (400 MPa), using a surface tension of 484 dyne/cm and a contact angle of 140°. The wetting angle was assumed to be equal to 140° by following the recommendations of the work "Techniques de l'ingénieur, traité analyse et caractérisation [Engineering Techniques, Analytical Treatise and Characterization]," pages 1050-1055, written by Jean Charpin and Bernard Rasneur.

So as to obtain better precision, the value of the total pore volume corresponds to the value of the total pore volume that is measured by mercury intrusion porosimetry that is measured on the sample minus the value of the total pore volume measured by mercury intrusion porosimetry measured on the same sample for a pressure that corresponds to 30 psi (approximately 0.2 MPa).

The volume of the macropores and mesopores is measured by mercury intrusion porosimetry according to the Standard ASTM D4284-83 at a maximum pressure of 4000 bar (400 MPa), using a surface tension of 484 dyne/cm and a contact angle of 140°. The value beyond which the mercury fills all of the intergranular gaps is set at 0.2 MPa, and it is considered that beyond this, the mercury penetrates into the pores of the sample.

The macropore volume of the catalyst or of the substrate that is used for the preparation of the catalyst according to the invention is defined as being the cumulative volume of mercury introduced at a pressure of between 0.2 MPa and 30 MPa, corresponding to the volume that is contained in the pores with an apparent diameter of greater than 50 nm.

The mesopore volume of the catalyst or of the substrate that is used for the preparation of the catalyst according to the invention is defined as being the cumulative volume of mercury that is introduced at a pressure of between 30 MPa and 400 MPa, corresponding to the volume that is contained in the pores with an apparent diameter of between 2 and 50 nm.

The volume of the micropores is measured by nitrogen porosimetry. The quantitative analysis of the microporosity is carried out starting from the method "t" (Lippens-De Boer Method, 1965), which corresponds to a transform of the initial adsorption isotherm as described in the work "Adsorption by Powders and Porous Solids. Principles, Methodology and Applications" written by F. Rouquérol, J. Rouquérol, and K. Sing, Academic Press, 1999.

The median mesopore diameter is also defined as being the diameter such that all of the pores, among all of the pores that constitute the mesopore volume, of a size less than this diameter constitute 50% of the total mesopore volume determined by mercury intrusion porosimetry.

The median macropore diameter is also defined as being the diameter such that all of the pores, among all of the pores that constitute the macropore volume, of a size that is less than this diameter constitute 50% of the total macropore volume that is determined by mercury intrusion porosimetry.

The specific surface area of the catalyst or of the substrate used for the preparation of the catalyst according to the invention is defined as the B.E.T. specific surface area that is determined by nitrogen adsorption in accordance with the Standard ASTM D 3663-78 established starting from the BRUNAUER-EMMETT-TELLER method that is described in the periodical "The Journal of American Society," 60, 309, (1938).

Below, the groups of chemical elements are provided according to the CAS classification (CRC Handbook of Chemistry and Physics, CRC Press Editor, Chief Editor D. R. Lide, 81$^{st}$ Edition, 2000-2001). For example, group VIII according to the CAS classification corresponds to the metals of columns 8, 9 and 10 according to the new IUPAC classification.

Characteristics of the Substrate According to the Invention

The majority of the substrate of the catalyst according to the invention comprises a calcined aluminum porous oxide.

Said substrate has a calcined alumina content that is greater than or equal to 90% by weight in relation to the total weight of said matrix, optionally completed by silica and/or phosphorus with a total content of at most 10% by weight of an equivalent of $SiO_2$ and/or $P_2O_5$, preferably less than 5% by weight, and in a very preferred manner less than 2% by weight in relation to the total weight of said matrix. The silica and/or the phosphorus can be introduced by any technique that is known to one skilled in the art, during the synthesis of the alumina gel or by impregnation of the substrate used for the preparation of the catalyst according to the invention.

In an even more preferred manner, the porous oxide substrate that for the most part is calcined aluminum consists of alumina.

In a preferred manner, the alumina that is present in said substrate is a transition alumina such as a gamma-, delta-, theta-, chi-, rho- or eta-alumina, by itself or in a mixture. In a more preferred manner, the alumina is a gamma, delta, or theta transition alumina, by itself or in a mixture.

The following characteristics of the substrate correspond to the characteristics of the substrate that is used for the preparation of the catalyst according to the invention before impregnation of the active phase.

The substrate that is used for the preparation of the catalyst according to the invention has a total pore volume of at least 0.33 mL/g, preferably between 0.36 and 1.3 mL/g, and in a particularly preferred manner between 0.40 and 1.2 mL/g.

The substrate that is used for the preparation of the catalyst according to the invention advantageously has a macropore volume of between 10 and 40% of the total pore volume of the substrate, preferably between 15 and 38% of the total pore volume of the substrate, and in an even more preferred manner between 20 and 35% of the total pore volume of the substrate.

The mesopore volume of the substrate that is used for the preparation of the catalyst according to the invention is at least 0.30 mL/g, preferably between 0.35 and 1.0 mL/g, and in a particularly preferred manner between 0.35 and 0.9 mL/g.

The substrate that is used for the preparation of the catalyst according to the invention advantageously has a pore volume of the pores that have a pore diameter of between 100 and 700 nm that is less than 20% of the total pore volume of the substrate, preferably less than 18% of the total pore volume of the substrate, and in a particularly preferred manner less than 15% of the total pore volume of the substrate.

The median mesopore diameter of the substrate that is used for the preparation of the catalyst according to the invention is between 8 nm and 25 nm, and preferably between 9 and 22 nm.

The substrate that is used for the preparation of the catalyst according to the invention has a median macropore diameter of greater than 200 nm, preferably between 250 and 1500 nm, preferably between 270 and 1000 nm, and in an even more preferred manner between 300 and 800 nm.

The substrate that is used for the preparation of the catalyst according to the invention has a B.E.T. specific surface area of at least 40 $m^2/g$, preferably at least 50 $m^2/g$, and in an even more preferred manner between 60 and 400 $m^2/g$.

When it is desired to use the catalyst according to the invention in a reaction for selective hydrogenation of polyunsaturated molecules such as diolefins, acetylenic compounds or alkenylaromatic compounds, the substrate that is used for the preparation of the catalyst according to the invention advantageously has a B.E.T. specific surface area of between 60 and 230 $m^2/g$.

When it is desired to use the catalyst according to the invention in a reaction for hydrogenation of aromatic compounds, the substrate that is used for the preparation of the catalyst according to the invention advantageously has a B.E.T. specific surface area of between 130 and 400 $m^2/g$.

Preferably, the substrate that is used for the preparation of the catalyst according to the invention has little microporosity; in a very preferred manner, it does not have any microporosity.

Characteristics of the Catalyst

The finished catalyst, i.e., with the active phase deposited on the substrate by any method that is known to one skilled in the art, as is described below, consequently has the textural properties given below.

The catalyst according to the invention has a total pore volume of at least 0.34 mL/g, preferably at least 0.37 mL/g, and in a particularly preferred manner between 0.40 and 0.9 mL/g.

The catalyst according to the invention advantageously has a macropore volume of between 10 and 40% of the total pore volume of the catalyst, preferably between 15 and 38% of the total pore volume of the catalyst, and in an even more preferred manner between 20 and 35% of the total pore volume of the catalyst.

The mesopore volume of the catalyst is at least 0.30 mL/g, preferably at least 0.35 mL/g, and in a particularly preferred manner between 0.35 mL/g and 0.8 mL/g.

The median mesopore diameter of the catalyst is between 8 nm and 25 nm, and preferably between 9 and 22 nm.

The catalyst has a median macropore diameter of greater than 200 nm, preferably between 250 and 1500 nm, preferably between 270 and 1000 nm, and in an even more preferred manner between 300 and 800 nm.

The catalyst according to this invention has a B.E.T. specific surface area of at least 40 $m^2/g$, preferably at least 50 $m^2/g$, and in an even more preferred manner between 55 and 250 $m^2/g$.

When it is desired to use the catalyst according to the invention in a reaction for selective hydrogenation of polyunsaturated molecules such as diolefins, acetylenic compounds or alkenylaromatic compounds, the catalyst according to the invention advantageously has a B.E.T. specific surface area of between 55 and 170 $m^2/g$.

When it is desired to use the catalyst according to the invention in a reaction for hydrogenation of aromatic compounds, the catalyst according to the invention advantageously has a B.E.T. specific surface area of between 90 and 250 $m^2/g$.

Preferably, the catalyst has little microporosity; in a very preferred manner, it does not have any microporosity.

The nickel content is between 5 and 65% by weight of said element in relation to the total mass of the catalyst, preferably between 8 and 55% by weight, in an even more preferred manner between 10 and 40% by weight, and in a particularly preferred manner between 10 and 34% by weight. The Ni content is measured by X fluorescence.

When it is desired to use the catalyst according to the invention in a reaction for selective hydrogenation of polyunsaturated molecules such as diolefins, acetylenic compounds or alkenylaromatic compounds, the nickel content is advantageously between 5 and 25% by weight, preferably between 8 and 25% by weight, and more preferably between 10 and 23% by weight of said element in relation to the total mass of the catalyst.

When it is desired to use the catalyst according to the invention in a reaction for hydrogenation of aromatic compounds, the nickel content is advantageously between 15 and 65% by weight, preferably between 18 and 55% by weight, and more preferably between 19 and 34% by weight of said element in relation to the total mass of the catalyst.

The size of the nickel particles in the catalyst according to the invention is less than 20 nm, preferably between 1.5 and 18 nm. The diameter of the nickel crystallites in oxide form is understood by "size of the nickel particles." The diameter of the nickel crystallites in oxide form is determined by X-ray diffraction, starting from the width of the diffraction line located at the 2theta angle=43° (i.e., in the crystallographic direction [200]), using the Scherrer equation. This method, which is used in X-ray diffraction on polycrystalline powders or samples and which connects the width at mid-height of the diffraction peaks to the size of the particles, is described in detail in the reference: Appl. Cryst. (1978), 11, 102-113 "Scherrer After Sixty Years: A Survey and Some New Results in the Determination of Crystallite Size," J. I. Langford and A. J. C. Wilson.

The active phase of the catalyst can also comprise at least one additional metal that is selected from among the metals of group VIII, the metals of group IB, and/or tin. In a preferred manner, the additional metal of group VIII is selected from among platinum, ruthenium, and rhodium, as well as palladium. Advantageously, the additional metal of group IB is selected from among copper, gold, and silver. Said additional metal(s) of group VIII and/or group IB is (are) preferably present with a content representing 0.01 to 20% by weight of the mass of the catalyst, preferably 0.05 to 10% by weight of the mass of the catalyst, and in an even more preferred manner 0.05 to 5% by weight of the mass of said catalyst. Tin is preferably present with a content that represents 0.02 to 15% by weight of the mass of the catalyst, in such a way that the Sn/Ni molar ratio is between 0.01 and 0.2, preferably between 0.025 to 0.055, and in an even more preferred manner between 0.03 to 0.05.

The active phase of the catalyst does not comprise metal from group VIB. It does not comprise in particular molybdenum or tungsten.

Said catalyst according to the invention is generally presented in all of the forms known by one skilled in the art, for example in the form of balls (generally having a diameter of between 1 and 6 mm), extrudates, tablets, hollow cylinders. Preferably, it consists of extrudates with a diameter that is generally between 0.5 and 10 mm, preferably between 0.8 and 3.2 mm, and in a very preferred manner between 1.0 and 2.5 mm. The former can advantageously be presented in the form of extrudates that are cylindrical, multilobed, trilobed or quadrilobed. Preferably, its shape will be trilobed or quadrilobed. The shape of the lobes can be adjusted according to all of the methods known from the prior art.

Preparation Method

This invention also has as its object a method for preparation of said catalyst according to the invention.

The catalyst according to the invention is prepared from a specific alumina gel. The particular pore distribution that is observed in the catalyst is in particular due to the method for preparation starting from the specific alumina gel.

The preparation of said alumina gel comprises the successive steps: a step for solubilization of an acid precursor of aluminum, a step for adjustment of the pH of the suspension by means of a basic precursor, and a step for co-precipitation of at least one acid precursor and at least one basic precursor, at least one of the two containing aluminum and a filtering step. The gel is then subjected to a drying step so as to obtain a powder. The powder is then either shaped and then subjected to a heat treatment, or first subjected to a heat treatment and then shaped so as to obtain a calcined aluminum porous oxide substrate in the two cases. The calcined aluminum porous oxide substrate is then impregnated with a solution that comprises the salt(s) of the precursor(s) of the active phase, and then dried to obtain a dried catalyst. Then, the dried catalyst is optionally subjected to a heat treatment, and then generally reduced and subjected to a passivation treatment.

More particularly, the method for preparation of the catalyst according to the invention comprises the following steps:

a) A step for solublization of an acid precursor of aluminum that is selected from among aluminum sulfate, aluminum chloride, and aluminum nitrate in water, at a temperature of between 20 and 90° C., at a pH of between 0.5 and 5, for a period of between 2 and 60 minutes, b) A step for adjustment of the pH by adding into the suspension that is obtained in step a) at least one basic precursor that is selected from among sodium aluminate, potassium aluminate, ammonia, sodium hydroxide, and potassium hydroxide, at a temperature of between 20 and 90° C., and at a pH of between 7 and 10, for a period of between 5 and 30 minutes, c) A step for co-precipitation of the suspension that is obtained at the end of step b) by adding into the suspension at least one basic precursor that is selected from among sodium aluminate, potassium aluminate, ammonia, sodium hydroxide, and potassium hydroxide, and at least one acid precursor that is selected from among aluminum sulfate, aluminum chloride, aluminum nitrate, sulfuric acid, hydrochloric acid, and nitric acid, at least one of the basic or acid precursors comprising aluminum, with the relative flow rate of the acid and basic precursors being selected in such a way as to obtain a pH of the reaction medium of between 7 and 10, and the flow rate of the acid and basic precursor(s) containing aluminum being regulated in such a way as to obtain a final alumina concentration in the suspension of between 10 and 38 g/L, d) A step for filtering the suspension that is obtained at the end of step c) of co-precipitation for obtaining an alumina gel, e) A step for drying said alumina gel that is obtained in step d) for obtaining a powder, f) A shaping step, g) A step of heat treatment carried out between steps e) and f) or after step f) at a temperature of between 500 and 1000° C., with or without the presence of an air stream containing up to 60% by volume of water for obtaining a calcined aluminum porous oxide substrate, h) A step for impregnating said substrate with a solution that comprises the salt(s) of the precursor(s) of the nickel-based active phase, i) A step for drying the impregnated substrate at a temperature of between 15 and less than 250° C., in such a way as to obtain a dried catalyst, j) Optionally a heat treatment of said dried catalyst at a temperature of between 250 and 1000° C. with or without the presence of water.

Step a) of Solubilization

Step a) is a step for solubilization of an acid precursor of aluminum that is selected from among aluminum sulfate, aluminum chloride, and aluminum nitrate in water, at a temperature of between 20 and 90° C., at a pH of between 0.5 and 5, for a period of between 2 and 60 minutes. Step a) is carried out at a temperature of between 20 and 90° C., in a preferred manner between 20 and 75° C., and in a more preferred manner between 30 and 70° C. The pH of the suspension that is obtained is between 0.5 and 5, preferably between 1 and 4, in a preferred manner between 1.5 and 3.5. This step advantageously contributes to a quantity of alumina that is introduced in relation to the final alumina of between 0.5 and 4%, preferably between 1 and 3%, in a very preferred manner between 1.5 and 2.5%. The suspension is left to stir for a period of between 2 and 60 minutes, and preferably of 5 to 30 minutes.

Step b) of Adjustment of the pH

Step b) of adjustment of the pH consists in the addition into the suspension that is obtained in step a) of at least one basic precursor that is selected from among sodium aluminate, potassium aluminate, ammonia, sodium hydroxide, and potassium hydroxide.

In a preferred manner, the basic precursor is selected from among sodium aluminate and potassium aluminate. In a very preferred manner, the basic precursor is sodium aluminate.

Step b) is carried out at a temperature of between 20 and 90° C., in a preferred manner between 20 and 80° C., and in a more preferred manner between 30 and 70° C., and at a pH of between 7 and 10, preferably between 8 and 10, in a preferred manner between 8.5 and 10, and in a very preferred manner between 8.7 and 9.9. The duration of step b) of adjustment of the pH is between 5 and 30 minutes, preferably between 8 and 25 minutes, and in a very preferred manner between 10 and 20 minutes.

Step c) of Co-Precipitation

Step c) is a step for co-precipitation of the suspension that is obtained at the end of step b) by adding into this suspension an aqueous solution of at least one basic precursor that is selected from among sodium aluminate, potassium aluminate, ammonia, sodium hydroxide, and potassium hydroxide, and at least one acid precursor that is selected from among aluminum sulfate, aluminum chloride, aluminum nitrate, sulfuric acid, hydrochloric acid, and nitric acid, with at least one of the basic or acid precursors comprising aluminum, said precursors being selected to be identical or not to the precursors that are introduced in steps a) and b). The relative flow rate of the acid and basic precursors being selected in such a way as to obtain a pH of the reaction medium of between 7 and 10 and the flow rate of the acid and basic precursor(s) containing aluminum being regulated in such a way as to obtain a final alumina concentration in the suspension of between 10 and 38 g/L, preferably between 13 and 35 g/L and more preferably between 15 and 33 g/L.

In a preferred manner, the co-precipitation step is conducted at a temperature of between 20 and 90° C., and in a more preferred manner between 30 and 70° C.

Step c) of co-precipitation is carried out at a pH of between 7 and 10, preferably between 8 and 10, in a preferred manner between 8.5 and 10, and in a very preferred manner between 8.7 and 9.9.

Step c) of co-precipitation is carried out for a period of between 1 and 60 minutes, and in a preferred manner between 5 and 45 minutes.

Preferably, said steps a), b), and c) are carried out in the absence of the organic additive. Preferably, steps a), b), and c) are performed while stirring is taking place.

Step d) of Filtering

The method for preparation of alumina according to the invention also comprises a step d) for filtering the suspension that is obtained at the end of step c) in such a way as to obtain an alumina gel.

Said filtering step is carried out according to the methods that are known to one skilled in the art.

Said filtering step is advantageously followed by at least one washing step, with an aqueous solution, preferably with water and preferably with one to three washing steps, with a quantity of water that is equal to the quantity of filtered precipitate.

Step e) of Drying of Alumina Gel

In accordance with the invention, the alumina gel that is obtained at the end of step c) of precipitation, followed by a step d) of filtering, is dried in a step e) of drying for obtaining a powder. Said drying step is generally implemented at a temperature of greater than or equal to 120° C. or by atomization or by any other drying technique known to one skilled in the art.

In the case where said step e) of drying is implemented by drying at a temperature that is greater than or equal to 120° C., said step d) [sic] of drying can advantageously be carried out in a closed and ventilated oven. Preferably, said drying step is performed at a temperature of between 120 and 300° C., in a very preferred manner at a temperature of between 150 and 250° C.

In the case where said step e) of drying is implemented by atomization, the "cake" obtained at the end of the second precipitation step, followed by a filtering step, is resuspended. Said suspension is then sprayed in fine droplets, into a vertical cylindrical chamber in contact with a hot air current so as to evaporate the water according to the principle that is well known to one skilled in the art. The powder that is obtained is entrained by the heat stream until it reaches a cyclone or a sleeve filter that will separate the air from the powder.

Preferably, in the case where said step e) of drying is implemented by atomization, the atomization is carried out according to the operating procedure described in the publication Asep Bayu Dani Nandiyanto, Kikuo Okuyama, Advanced Powder Technology, 22, 1-19, 2011.

Step f) Shaping

In accordance with the invention, step f) of shaping is then carried out.

According to a first, preferred, variant, the powder that is obtained at the end of step e) for drying alumina gel is shaped according to step f), and then the powder that is shaped at the end of step f) is subjected to a heat treatment according to step g) that is described below for obtaining a calcined aluminum porous oxide substrate.

According to a second variant, the powder that is obtained at the end of step e) for drying alumina gel is first subjected to a heat treatment according to step g) that is described below, and then shaped according to step f) for obtaining a calcined aluminum porous oxide substrate.

Preferably, said step f) of shaping is carried out according to any technique that is known to one skilled in the art, for example the methods of shaping by extrusion, by pelletization, by the oil-drop method (draining), or by turntable granulation.

In a very preferred manner, said step f) of shaping is carried out by extrusion. It is possible to use a piston extruder through a die that has the desired diameter, typically between 0.5 and 10 mm. The extrudates generally have a diameter of between 0.5 and 10 mm, preferably 0.8 and 3.2 mm, and in a very preferred manner between 1.0 and 2.5 mm. The extrudates can advantageously be presented in the form of extrudates that are cylindrical, multilobed, trilobed, or quadrilobed. Preferably, the shape will be trilobed or quadrilobed.

Any other element, for example silica in the form of a solution or an emulsion of silicic precursor, can be introduced during the shaping.

Step 2) Heat Treatment

In accordance with the invention, a heat treatment step is carried out between steps e) and f) or after step f) at a temperature of between 500 and 1000° C., with or without the presence of an air stream containing up to 60% by volume of water for obtaining a calcined aluminum porous oxide.

According to the first, preferred, variant, the heat treatment step is carried out after step f) of shaping. In this case, the heat treatment step can be preceded by a drying at a temperature of between 50° C. and 200° C., according to any technique that is known to one skilled in the art.

According to a second variant, the heat treatment step is carried out between step e) for drying the alumina gel, and step f) of shaping.

Preferably, said step g) of heat treatment is performed at a temperature of between 540 and 850° C. Preferably, said step g) of heat treatment is performed for a period of between 2 and 10 hours.

"Heat treatment" is defined as the temperature treatment respectively without the presence or with the presence of water. In this latter case, the contact with water vapor can take place at atmospheric pressure ("steaming") or with autogenous pressure (autoclaving). Multiple cycles combined without the presence or with the presence of water can be carried out.

In the case of the presence of water, the water content is preferably between 150 and 900 grams per kilogram of dry air, and, in an even more preferred manner, between 250 and 650 grams per kilogram of dry air.

Said step g) of heat treatment makes possible the transition of alumina gel, also called boehmite, to the calcined aluminum porous oxide substrate that has the textural characteristics as described above. The alumina has a crystallographic structure of a transition alumina such as gamma, delta, theta, chi, rho or eta, by itself or in a mixture. In a more preferred manner, the alumina is a gamma, delta or theta transition alumina, by itself or in a mixture. The existence of the different crystallographic structures is linked to the conditions of implementing step g) of heat treatment.

Step h) Impregnation of the Active Phase

According to step h) of the method according to the invention, the calcined aluminum porous oxide substrate is impregnated with a solution that comprises the salt(s) of the precursor(s) of the nickel-based active phase.

The active phase is provided by one or more solutions that contain at least nickel.

Said solution(s) can be aqueous or consist of an organic solvent or else a mixture of water and at least one organic solvent (for example, ethanol or toluene). Preferably, the solution is aqueous. The pH of this solution can be modified by the optional addition of an acid. According to another preferred variant, the aqueous solution can contain ammonia or $NH_4^+$ ammonium ions.

In a preferred manner, said nickel precursor is introduced into aqueous solution, for example in the form of nitrate, carbonate, acetate, chloride, hydroxide, hydroxycarbonate, oxalate, complexes formed by a polyacid or an acid-alcohol and its salts, complexes formed with the acetylacetonates, or any other inorganic derivative that is soluble in aqueous solution, which is brought into contact with said calcined aluminum porous oxide. In a preferred manner, nickel nitrate, nickel chloride, nickel acetate or nickel hydroxycarbonate is advantageously used as a nickel precursor. In a very preferred manner, the nickel precursor is nickel nitrate or nickel hydroxycarbonate.

According to another preferred variant, said nickel precursor is introduced into ammoniacal solution by introducing a nickel salt, for example nickel hydroxide or nickel carbonate in an ammoniacal solution or in a solution of ammonium carbonate or ammonium bicarbonate.

The quantities of the nickel precursor(s) introduced into the solution are selected in such a way that the total nickel content is between 5 and 65% by weight, preferably between 8 and 55% by weight, in a preferred manner between 10 and 40% by weight, and in a particularly preferred manner between 10 and 34% by weight of said element in relation to the total mass of the catalyst. The nickel contents are generally adapted to the targeted hydrogenation reaction as described above in the paragraph of the description of the catalyst.

Any other additional element can be introduced at the time of this step:

When it is desired to introduce phosphorus, a phosphoric acid solution can be introduced into the impregnation solution.

When it is desired to introduce an additional metal that is selected from among the metals of group VIII, the metals of group IB and/or tin, a salt that is selected from among nitrate, sulfate, chloride or any other conventional precursor is advantageously used as a precursor.

An additive, for example a chelating agent of organic nature, can advantageously be introduced into the solution if one skilled in the art deems it necessary.

The impregnation of the active phase can be carried out according to all of the methods that are known to one skilled in the art, in particular by dry impregnation. In a preferred way, nickel, and optionally at least one supplementary element such as an additional metal that is selected from among the metals of group VIII, the metals of group IB, and/or tin, phosphorus, or an additive such as a chelating agent of an organic nature are deposited by dry impregnation of their associated precursors on the oxide substrate according to the invention.

The deposition can be done via a single dry impregnation step of the oxide substrate according to the invention via the use of a solution that simultaneously contains at least one nickel compound, and optionally at least one supplementary element.

The deposition can also advantageously be done via at least two dry impregnation cycles. The different elements can thus be advantageously successively impregnated or else one of the elements can also be impregnated in multiple sequences. One of the impregnations that is carried out can make it possible in particular to introduce an organic compound in addition to the active phase of the catalyst. In these cases, each impregnation is advantageously followed by drying and optionally a heat treatment. The drying can be done at a temperature of between 15 and 250° C., preferably between 80 and 200° C., generally for a period of between 10 minutes and 24 hours. The heat treatment can be done at a temperature of between 200 and 1000° C., preferably between 250 and 750° C., generally for a period of between 15 minutes and 10 hours.

Step i) Drying of the Impregnated Substrate

In accordance with the invention, the impregnated substrate that is obtained at the end of step h) of impregnation of the active phase undergoes a step i) of drying at a temperature of between 15 and less than 250° C., preferably between 80 and 200° C., according to any technique that is known to one skilled in the art, for a period that is typically between 10 minutes and 24 hours. A dried catalyst is obtained.

Step j) Heat Treatment of the Dried Catalyst

The thus dried catalyst can then undergo a complementary step j) of heat treatment at a temperature of between 250 and 1000° C. and preferably between 250 and 750° C., for a period that is typically between 15 minutes and 10 hours, with or without the presence of water.

"Heat treatment" is defined as the temperature treatment respectively without or with the presence of water. In this latter case, the contact with the water vapor can take place at atmospheric pressure ("steaming") or under autogenous pressure (autoclaving). Multiple combined cycles of hydrothermal or heat treatments can be carried out. After this or these treatment(s), the catalyst precursor comprises nickel in oxide form, i.e., in NiO form.

In the case of hydrothermal treatment, the water content is preferably between 150 and 900 grams per kilogram of dry air, and in an even more preferred manner, between 250 and 650 grams per kilogram of dry air.

Step k) Reduction by a Reducing Gas

Prior to the use of the catalyst in the catalytic reactor and the implementation of a hydrogenation method, at least one step k) of reducing treatment is advantageously carried out in the presence of a reducing gas after steps i) or j) in such a way as to obtain a catalyst that comprises nickel that is at least partially in metallic form.

This treatment makes it possible to activate said catalyst and to form metal particles, in particular nickel in the zero-valent state. Said reducing treatment can be carried out in-situ or ex-situ, i.e., after or before the loading of the catalyst into the hydrogenation reactor. Said step k) of reducing treatment can be implemented on the catalyst that may or may not have been subjected to step l) of passivation, described below.

The reducing gas is preferably hydrogen. The hydrogen can be used in pure form or in a mixture (for example, a mixture of hydrogen/nitrogen, hydrogen/argon, hydrogen/methane). In the case where hydrogen is used in a mixture, all of the proportions can be considered.

Said reducing treatment is carried out at a temperature of between 120 and 500° C., preferably between 150 and 450° C. When the catalyst does not undergo passivation or undergoes a reducing treatment before passivation, the reducing treatment is carried out at a temperature of between 350 and 500° C., preferably between 350 and 450° C. When the catalyst has undergone passivation in advance, the reducing treatment is generally carried out at a temperature of between 120 and 350° C., preferably between 150 and 350° C.

The duration of the reducing treatment is generally between 2 and 40 hours, preferably between 3 and 30 hours. The rise in temperature to the desired reduction temperature is generally slow, for example set between 0.1 and 10° C./minute, preferably between 0.3 and 7° C./minute.

The flow rate of hydrogen, expressed in terms of L/hour/gram of catalyst, is between 0.1 and 100 L/hour/gram of catalyst, preferably between 0.5 and 10 L/hour/gram of catalyst, in an even more preferred way between 0.7 and 5 L/hour/gram of catalyst.

Step l) Passivation

Prior to its implementation in the catalytic reactor, the catalyst according to the invention can optionally undergo a passivation step (step l) by a sulfur-containing compound or an oxidized compound or by $CO_2$ before or after step k) of reducing treatment. This passivation step can be carried out ex-situ or in-situ. The passivation step is carried out by the implementation of methods that are known to one skilled in the art.

The sulfur passivation step makes it possible to improve the selectivity of catalysts and to prevent heat excursions during start-ups of new catalysts ("run away" according to English terminology). The passivation generally consists in irreversibly poisoning, by the sulfur-containing compound, the most virulent active sites of nickel that exist in the new catalyst and therefore in minimizing the activity of the catalyst to benefit its selectivity. The passivation step is carried out by implementing methods that are known to one skilled in the art and in particular, by way of example, by implementing one of the methods described in the documents of patents EP0466567, U.S. Pat. No. 5,153,163, FR2676184, WO2004/098774, EP0707890. The sulfur-containing compound is selected from among, for example, the following compounds: thiophene, thiophane, alkyl monosulfides such as dimethyl sulfide, diethyl sulfide, dipropyl sulfide, and propyl methyl sulfide or else an organic disulfide of formula HO—$R_1$—S—S—$R_2$—OH such as the di-thio-di-ethanol of formula HO—$C_2H_4$—S—S—$C_2H_4$—OH (often called DEODS). The sulfur content is generally between 0.1 and 2% by weight of said element in relation to the mass of the catalyst.

The step of passivation by an oxidized compound or by $CO_2$ is generally carried out after a reducing treatment in advance at a high temperature, generally between 350 and 500° C., and it makes it possible to preserve the metal phase of the catalyst in the presence of air. A second reducing treatment at a lower temperature generally between 120 and 350° C. is then generally carried out. The oxidized compound is generally air or any other stream that contains oxygen.

Selective Hydrogenation Method

This invention also relates to the use of the catalyst according to the invention in a hydrogenation method and in particular in a method for selective hydrogenation of polyunsaturated molecules such as diolefins, acetylenic compounds, or alkenylaromatic compounds, also called styrene compounds.

The mono-unsaturated organic compounds, such as, for example, ethylene and propylene, are at the source of the manufacturing of polymers, plastic materials, and other value-added chemical products. These compounds are obtained from natural gas, naphtha, or diesel fuel, which have been treated by steam-cracking or catalytic-cracking methods. These methods are performed at high temperature and produce, in addition to desired mono-unsaturated compounds, polyunsaturated organic compounds such as acetylene, propadiene, and methylacetylene (or propyne), 1,2-butadiene, and 1,3-butadiene, vinylacetylene, and ethylacetylene, and other polyunsaturated compounds whose boiling point corresponds to the C5+ gasoline fraction (gasolines that contain hydrocarbon compounds that have 5 or more carbon atoms), in particular diolefinic or styrene or indene compounds. These polyunsaturated compounds are very reactive and lead to parasitic reactions in the polymerization units. It is therefore necessary to eliminate them before upgrading these fractions.

The selective hydrogenation is the main treatment that is developed for eliminating specifically the undesirable polyunsaturated compounds from these hydrocarbon feedstocks. It makes possible the conversion of polyunsaturated compounds to the corresponding alkenes or aromatic compounds by preventing their total saturation and therefore the formation of corresponding alkanes or naphthenes. In the case of steam-cracking gasolines used as feedstock, the selective hydrogenation also makes it possible to hydrogenate selectively the alkenylaromatic compounds into aromatic compounds by preventing the hydrogenation of the aromatic cores.

The hydrocarbon feedstock that is treated in the selective hydrogenation method has a final boiling point that is less than or equal to 250° C. and that contains at least 2 carbon atoms per molecule and comprises at least one polyunsaturated compound. "Polyunsaturated compounds" are defined as compounds that comprise at least one acetylene group and/or at least one diene group and/or at least one alkenylaromatic group.

More particularly, the feedstock is selected from the group that consists of a C2 steam-cracking fraction, a C3 steam-cracking fraction, a C4 steam-cracking fraction, a C5 steam-cracking fraction, and a steam-cracking gasoline that is also called pyrolysis gasoline. The steam-cracking gasoline or pyrolysis gasoline corresponds to a hydrocarbon fraction whose boiling point is generally between 0 and 250° C., preferably between 10 and 220° C. The polyunsaturated hydrocarbons that are to be hydrogenated and that are present in said steam-cracking gasoline are in particular diolefinic compounds (butadiene, isoprene, cyclopentadiene . . . ), styrene compounds (styrene, alpha-methylstyrene . . . ) and indene compounds (indene . . . ). The steam-cracking gasoline generally comprises the C5-C12 fraction with traces of C3, C4, C13, C14, C15 (for example, between 0.1 and 3% by weight for each of these fractions). For example, a feedstock that is formed from pyrolysis gasoline generally has the following composition: 5 to 25% by weight of paraffins, 40 to 70% by weight of aromatic compounds, 5 to 20% by weight of monoolefins, 5 to 40% by weight of diolefins, 1 to 10% by weight of alkenylaromatic compounds, and 20 to 300 ppm by weight of sulfur, with all of the compounds forming 100%. In a preferred manner, the polyunsaturated hydrocarbon feedstock that is treated in accordance with the selective hydrogenation method according to the invention is a steam-cracking gasoline.

The purpose of the selective hydrogenation method according to the invention is to eliminate said polyunsaturated hydrocarbons that are present in said feedstock to be hydrogenated without hydrogenating the monounsaturated hydrocarbons. For example, when said feedstock is a C2 fraction, the purpose of the selective hydrogenation method is to hydrogenate acetylene selectively. When said feedstock is a C3 fraction, the purpose of the selective hydrogenation method is to hydrogenate propadiene and methylacetylene selectively. In the case of a C4 fraction, the purpose is to eliminate butadiene, vinylacetylene (VAC), and butyne; in the case of a C5 fraction, the purpose is to eliminate the pentadienes. When said feedstock is a steam-cracking gasoline, the purpose of the selective hydrogenation method is to hydrogenate selectively said polyunsaturated hydrocarbons that are present in said feedstock to be treated in such a way that the diolefinic compounds are partially hydrogenated into monoolefins and the styrene and indene compounds are partially hydrogenated into corresponding aromatic compounds by preventing the hydrogenation of the aromatic cores.

The technological implementation of the selective hydrogenation method is carried out by, for example, injection, upward or downward, of the polyunsaturated hydrocarbon feedstock and hydrogen in at least one fixed-bed reactor. Said reactor can be of the isothermal type or of the adiabatic type. An adiabatic reactor is preferred. The polyunsaturated hydrocarbon feedstock can advantageously be diluted by one or more re-injection(s) of effluent, obtained from said reactor where the selective hydrogenation reaction occurs, at various points of the reactor, located between the inlet and the outlet of the reactor so as to limit the temperature gradient in the reactor. The technological implementation of the selective hydrogenation method according to the invention can also be advantageously carried out by the installation of at least said supported catalyst in a reactive distillation column or in reactors-exchangers. The hydrogen stream can be introduced at the same time as the feedstock that is to be hydrogenated and/or at one or more different points of the reactor.

The selective hydrogenation of the C2, C3, C4, C5 and C5+ fractions can be carried out in the gaseous phase or in the liquid phase, preferably in the liquid phase for the C3, C4, C5 and C5+ fractions. Actually, a liquid-phase reaction makes it possible to lower the energy cost and to increase the service life of the catalyst.

In a general manner, the selective hydrogenation is carried out at a temperature of between 0 and 500° C., at a pressure of between 0.1 and 20 MPa, at a hydrogen/(polyunsaturated compounds to be hydrogenated) molar ratio of between 0.1 and 10, and at an hourly volumetric flow V.V.H. (defined as the ratio of the volumetric flow rate of feedstock to the volume of catalyst) of between 0.1 and 200 $h^{-1}$ for a liquid feedstock, between 100 and 15000 $h^{-1}$ for a gaseous feedstock of a hydrocarbon feedstock that contains polyunsaturated compounds that contain at least 2 carbon atoms per molecule and that have a final boiling point that is less than or equal to 250° C.

In a preferred manner, a selective hydrogenation method is carried out in which the feedstock is a steam-cracking gasoline that comprises polyunsaturated compounds; the (hydrogen)/(polyunsaturated compounds to be hydrogenated) molar ratio is generally between 1 and 2; the temperature is generally between 40 and 200° C., preferably between 50 and 180° C.; the hourly volumetric flow rate (V.V.H.) is generally between 0.5 and 50 $h^{-1}$, preferably between 1 and 20 $h^{-1}$, and the pressure is generally between 0.3 and 6.5 MPa, preferably between 2.0 and 3.5 MPa. The hydrogen flow rate is adjusted so as to use a sufficient quantity of it theoretically to hydrogenate all of the polyunsaturated compounds and to maintain excess hydrogen at the reactor outlet.

Method for Hydrogenation of Aromatic Compounds

This invention also relates to the use of the catalyst according to the invention in a hydrogenation method and in particular in a method for hydrogenation of aromatic compounds making it possible to transform the aromatic compounds of petroleum or petrochemical fractions by conversion of aromatic cores into naphthene cores.

The hydrocarbon feedstock that is treated in the method for hydrogenation of aromatic compounds has a final boiling point that is less than or equal to 650° C., generally between 20 and 650° C., and preferably between 20 and 450° C., and it contains at least one aromatic or polyaromatic compound. As a petroleum or petrochemical fraction that contains aromatic compounds, it is possible to cite, for example, kerosene, light diesel fuel, heavy diesel fuel, and cracking distillates, such as FCC recycling oil, coking unit diesel fuel, hydrocracking distillates, and the reformate from catalytic reforming.

The content of aromatic hydrocarbons in a feedstock that is treated in the hydrogenation method is generally between 0.1 and 80% by weight, preferably between 1 and 50% by weight, and in a particularly preferred manner between 2 and 35% by weight, with the percentage by weight being based on the total weight of the hydrocarbon feedstock. The aromatic compounds that are present are, for example, benzene or alkylaromatic compounds such as toluene, ethylbenzene, o-xylene, m-xylene, or p-xylene, or else aromatic compounds that have multiple aromatic (polyaromatic) cores, such as naphthalene.

The sulfur or chlorine content of the feedstock is generally less than 5000 ppm by weight of sulfur or chlorine respectively, preferably less than 100 ppm by weight, and in a particularly preferred manner less than 10 ppm.

The technological implementation of the method for hydrogenation of aromatic compounds can be carried out like the one described in the selective hydrogenation part.

The hydrogenation of aromatic compounds can be carried out in the gaseous phase or in the liquid phase, preferably in the liquid phase. In a general manner, the hydrogenation of the aromatic compounds is performed at a temperature of between 30 and 350° C., preferably between 50 and 325° C., at a pressure of between 0.1 and 20 MPa, preferably between 0.5 and 10 MPa, at a hydrogen/(aromatic compounds to be hydrogenated) molar ratio of between 0.1 and 10, and at an hourly volumetric flow rate V.V.H. of between 0.05 and 50 $h^{-1}$, preferably between 0.1 and 10 $h^{-1}$ of a hydrocarbon feedstock that contains aromatic compounds and that has a final boiling point that is less than or equal to 650° C. The flow rate of hydrogen is adjusted so as to use a sufficient quantity of it theoretically to hydrogenate all of the polyunsaturated compounds and to maintain excess hydrogen at the reactor outlet.

The conversion of the aromatic or polyaromatic compounds is generally greater than 20 mol %, preferably greater than 40 mol %, in a more preferred manner greater than 80 mol %, and in a particularly preferred manner greater than 90 mol % of the aromatic or polyaromatic compounds that are contained in the hydrocarbon feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a particular variant, the catalyst according to the invention is used in a method for hydrogenation of a hydrocarbon feedstock that contains benzene, such as, for example, the reformate that is obtained from a catalytic reforming unit. The benzene content is generally between 0.1 and 40% by weight, preferably between 0.5 and 35% by weight, and in a particularly preferred manner between 2 and 30% by weight, with the percentage by weight being based on the total weight of the hydrocarbon feedstock.

The sulfur or chlorine content of the feedstock is generally less than 10 ppm by weight of sulfur or chlorine respectively, and preferably less than 2 ppm by weight.

The hydrogenation of the feedstock that contains benzene can be carried out in the gaseous phase or in the liquid phase, preferably in the liquid phase. When it is carried out in the liquid phase, a solvent can be present. In a general manner, the hydrogenation of benzene is carried out at a temperature of between 30 and 250° C., preferably between 50 and 200° C., and in a more preferred manner between 80 and 180° C., at a pressure of between 0.1 and 10 MPa, preferably between 0.5 and 4 MPa, with a hydrogen/(benzene) molar ratio of between 0.1 and 10, and at an hourly volumetric flow rate V.V.H. of between 0.05 and 50 $h^{-1}$, preferably between 0.5 and 10 $h^{-1}$.

The conversion of benzene is generally greater than 50 mol %, preferably greater than 80 mol %, in a more preferred manner greater than 90 mol %, and in a particularly preferred manner greater than 98 mol %.

The invention is illustrated by the following examples.

EXAMPLES

Example 1: Preparation of an Aqueous Solution of Ni Precursors

The aqueous solution of Ni precursors (solution S) that is used for the preparation of catalysts A, A', B, and C is prepared by dissolving 46.1 g of nickel nitrate (NiNO$_3$, supplier Strem Chemicals®) in a volume of 13 mL of distilled water. The solution S whose NiO concentration is 20.1% by weight (in relation to the mass of the solution) is obtained.

Example 2: Preparation of Catalysts A and A', According to the Invention

The catalysts A and A' according to the invention are prepared by dry impregnation of the solution S of Ni precursors on an alumina A1 and on an alumina A2. The goal is a content of 20% by weight of nickel in relation to the total mass of the catalyst A or A'.

The synthesis of the alumina A1 according to the invention is carried out in a laboratory reactor with a capacity of approximately 7000 mL. The synthesis takes place at 70° C. and while being stirred, in seven steps, named a) to g) below. An attempt is made to prepare 5 L of solution at a concentration fixed at 27 g/L of alumina in the final suspension (obtained at the end of step c) and with a contribution rate of the first step (a) at 2.1% of the total alumina.

a) Solubilization: In a single operation, 70 mL of aluminum sulfate Al$_2$(SO$_4$)$_3$ is introduced into the reactor that contains a foot of water of 1679 mL. The change in pH, which remains between 2.5 and 3, is followed for 10 minutes. This step contributes to the introduction of 2.1% of alumina in relation to the total mass of alumina that is formed at the end of the synthesis of the gel. The solution is left to stir for a period of 10 minutes.

b) Adjustment of the pH: Approximately 70 ml of sodium aluminate NaAlOO is gradually added. The objective is to reach a pH of between 7 and 10 in a period of 5 to 15 minutes.

c) Co-precipitation: In the suspension that is obtained at the end of step b), the following are added in 30 minutes:
  1020 mL of aluminum sulfate Al$_2$(SO$_4$)$_3$, or a flow rate of 34 mL/minute,
  1020 mL of sodium aluminate NaAlOO, or a flow rate of 34 mL/minute,
  1150 mL of distilled water, or a flow rate of 38.3 mL/minute.
The pH is between 8.7 and 9.9.

d) Filtering: The suspension that is obtained at the end of step c) is filtered by movement on a P4 sintered Buchner-type tool and washed multiple times with distilled water. An alumina gel is obtained.

e) Drying: The alumina gel that is obtained at the end of step d) is dried in the oven for one night at 200° C.

f) Heat treatment: The dried alumina gel that is obtained at the end of step e) is then calcined at 750° C. under a stream of air of 1 L/h/g of alumina at 750° C. for 2 hours (temperature rise slope of 5° C./minute).

g) Shaping: Shaping is carried out using a "Brabender"-type mixer with an acid level of 1% (total acid level, expressed in relation to the dry alumina), a neutralization rate of 20%, and acid and basic fire losses respectively of 62% and 64%. Then, the extrusion is carried out on a piston extruder through a trilobed die with a 2.1 mm diameter. After extrusion, the extrudates are dried for one night at 80° C. The alumina A1 is then obtained.

The characteristics of the alumina A1 thus obtained are recorded in Table 1 below.

The catalyst A is then prepared by dry impregnation of the solution S of Ni precursors, described in Example 1, on the alumina A1 according to the three steps, named h) to i) below:

h) A dry impregnation of the alumina A1 by adding drop-by-drop a volume of 11.5 mL of solution S to a mass of 10.5 g of the alumina A1, for a period of 10 minutes.

i) Drying of the catalytic precursor that is obtained at the end of step h) in the oven at 120° C. for one night.

j) A heat treatment by calcination of the catalyst that is dried under a stream of air of 1 L/h/g of catalyst, at 450° C. for 2 hours (temperature rise slope of 5° C./minute).

The calcined catalyst A is then obtained.

The characteristics of the calcined catalyst A that is thus obtained are recorded in Table 2 below.

The synthesis of the alumina A2 is carried out by following the steps a) to e) of the synthesis of the alumina A1. The operating conditions are strictly identical for these steps. After the drying of step e), first a shaping, and then a heat treatment are carried out in the following way:

f) Shaping: The dried alumina gel that is obtained from step e) is shaped using a "Brabender"-type mixer with an acid level of 1% (total acid level, expressed in relation to the dry alumina), a neutralization rate of 20%, and acid and basic fire losses respectively of 62% and 64%. Then, the extrusion is carried out on a piston extruder through a trilobed die with a 2.1 mm diameter. After extrusion, the extrudates are dried for one night at 80° C.

g) Heat treatment: The extrudates that are obtained at the end of step f) are then calcined at 750° C. under a stream of air of 1 L/h/g of alumina at 750° C. for 2 hours (temperature rise slope of 5° C./minute). The alumina A2 is then obtained.

The characteristics of the alumina A2 that is thus obtained are recorded in Table 1 below.

The catalyst A' is then prepared by dry impregnation of the solution S of Ni precursors, described in Example 1, on the alumina A2 according to the three steps h), i) and j) that are described above for the synthesis of the catalyst A, with the operating conditions being strictly identical.

The characteristics of the calcined catalyst A' that is thus obtained are recorded in Table 2 below.

TABLE 1

Properties of Aluminas A1 and A2 (According to the Invention), and B1 and C1 (For Comparison)

| | ALUMINAS | | | |
|---|---|---|---|---|
| | A1 According to the Invention | A2 According to the Invention | B1 For Comparison | C1 For Comparison |
| B.E.T. Surface Area ($m^2/g$) | 225 | 175 | 180 | 298 |
| Total Pore Volume (mL/g) | 0.94 | 0.97 | 0.82 | 0.57 |
| Mesopore Volume (mL/g) | 0.67 | 0.75 | 0.63 | 0.55 |
| Median Mespore Diameter (nm) | 12.5 | 17 | 13.0 | 17 |
| Macropore Volume (mL/g) | 0.27 | 0.22 | 0.19 | 0 |
| Macropore Volume (% of the Total Pore Volume) | 29 | 23 | 23 | 0 |
| Median Macropore Diameter (nm) | 644 | 353 | 143 | No Macroporosity |
| Pore volume of the pores that have a pore diameter of between 100 and 700 nm (mL/g and % of the total pore volume) | 0.07 8% | 0.01 5% | 0.12 14.5% | 0 0% |
| Micropore Volume (mL/g) | 0 | 0 | 0 | 0 |

TABLE 2

Properties of Catalysts A and A' (According to the Invention), and B and C (For Comparison)

| | CATALYSTS | | | |
|---|---|---|---|---|
| | A According to the Invention | A' According to the Invention | B For Comparison | C For Comparison |
| Ni (% by Weight) | 20.7 | 20.6 | 19.4 | 21.0 |
| B.E.T. Surface Area ($m^2/g$) | 156 | 121 | 119 | 206 |
| Total Pore Volume (mL/g) | 0.66 | 0.67 | 0.62 | 0.47 |
| Mesopore Volume (mL/g) | 0.47 | 0.53 | 0.48 | 0.47 |
| Median Mesopore Diameter (nm) | 11.5 | 15.6 | 10.5 | 10.5 |
| Macropore Volume (mL/g and % of the Total Pore Volume) | 0.19 29% | 0.14 21% | 0.14 23% | 0 0% |
| Median Macropore Diameter (nm) | 638 | 346 | 132 | No Macroporosity |
| Micropore Volume (mL/g) | 0 | 0 | 0 | 0 |
| Size of the NiO Crystallites (nm) | 15.6 | 16.2 | 14.1 | 11.0 |

Example 3: Preparation of the Catalyst B that has a Different Pore Distribution (for Comparison)

The catalyst B is prepared by dry impregnation of the solution S of Ni precursors by aiming at a content of 20% by weight of nickel in relation to the total mass of the catalyst on an alumina B1 that has a different pore distribution from that of the alumina A1 that is described in Example 2 above. The characteristics of this alumina B1 are recorded in Table 1. In particular, this alumina B1 has a macropore volume that is less than that of the alumina A1 and a median macropore diameter that is much smaller than that of the alumina A1.

The catalyst B is then prepared by dry impregnation of the solution S of Ni precursors, described in Example 1, on the alumina B1 according to the three steps, steps h) to i), of Example 2 described above. The operating conditions are strictly identical. The calcined catalyst B is then obtained.

The characteristics of the calcined catalyst B that is thus obtained are recorded in Table 2. It has a macropore volume that is smaller than that of the catalyst A and a median macropore diameter that is much smaller than that of the catalyst A. In addition, it has NiO crystallites that are slightly smaller than those of the catalyst A.

Example 4: Preparation of the Catalyst C that has a Different Pore Distribution (for Comparison)

The catalyst C is prepared by dry impregnation of the solution S of Ni precursors by aiming at a content of 20% by weight of nickel in relation to the total mass of the catalyst on an alumina C1 that has a pore distribution that is also different from that of the alumina A1 that is described in Example 2 above. The characteristics of this alumina C1 are recorded in Table 1. In particular, this alumina C1 does not have macroporosity.

The catalyst C is then prepared by dry impregnation of the solution S of Ni precursors, described in Example 1, on the alumina C1. In this alumina of small pore volume, two successive impregnations have been necessary for reaching an Ni content of approximately 20% by weight; the linking of the three steps h) to j) of Example 2 described above was then repeated twice (according to the sequence h, i, j, h, i, j). The first impregnation step makes it possible to obtain a content of 13% by weight of nickel; the second impregnation step makes it possible to reach a content of 21% by weight of nickel in relation to the total mass of the catalyst. For each step, the operating conditions are strictly identical to those described in Example 2 above. The calcined catalyst C is then obtained.

The characteristics of the calcined catalyst C that is thus obtained are recorded in Table 2. This catalyst does not have macroporosity. In addition, it has NiO crystallites that are smaller than those of the catalyst A.

Example 5: Evaluation of the Catalytic Properties of the Catalysts A, A', B and C with Regard to Selective Hydrogenation of a Mixture that Contains Styrene and Isoprene The catalysts A, A', B and C that are described in the examples above are tested with regard to the reaction for selective hydrogenation of a mixture that contains styrene and isoprene.

The composition of the feedstock that is to be selectively hydrogenated is as follows: 8% by weight of styrene (supplier Sigma Aldrich®, purity 99%), 8% by weight of isoprene (supplier Sigma Aldrich®, purity 99%), 84% by weight of n-heptane (solvent) (supplier VWR®, purity>99% HPLC Chromanorm). This feedstock also contains sulfur-containing compounds of very low content: 10 ppm by weight of sulfur introduced in the form of pentanethiol (supplier Fluka®, purity>97%) and 100 ppm by weight of sulfur introduced in the form of thiophene (supplier Merck®, purity 99%). This composition corresponds to the initial composition of the reaction mixture. This mixture of model molecules is representative of a pyrolysis gasoline.

The selective hydrogenation reaction is performed in a 500-mL stainless steel autoclave, equipped with a mechanical stirrer with a magnetic drive and able to operate under a maximum pressure of 100 bar (10 MPa) and temperatures of between 5° C. and 200° C.

Prior to its introduction into the autoclave, a quantity of 3 mL of catalyst is reduced ex situ under a stream of hydrogen of 1 L/h/g of catalyst, at 400° C. for 16 hours (temperature rise slope of 1° C./minute), and then it is transferred into the autoclave, in the absence of air. After adding 214 mL of n-heptane (supplier VWR®, purity>99% HPLC Chromanorm), the autoclave is closed, purged, and then pressurized under 35 bar (3.5 MPa) of hydrogen, and brought to the temperature of the test that is equal to 30° C. At time t=0, approximately 30 g of a mixture that contains styrene, isoprene, n-heptane, pentanethiol, and thiophene is introduced into the autoclave. The reaction mixture then has the composition that is described above, and stirring is begun at 1600 rpm. The pressure is kept constant at 35 bar (3.5 MPa) in the autoclave using a reservoir bottle that is located upstream from the reactor.

The progression of the reaction is followed by the taking of samples from the reaction medium at regular time intervals: styrene is hydrogenated into ethylbenzene, without hydrogenation of the aromatic cycle, and isoprene is hydrogenated into methylbutenes. If the reaction is extended longer than necessary, the methylbutenes in turn are hydrogenated into isopentane. The hydrogen consumption is also followed over time by the reduction in pressure in a reservoir bottle located upstream from the reactor. The catalytic activity is expressed in terms of moles of $H_2$ consumed per minute and per gram of Ni.

The catalytic activities that are measured for the catalysts A, A', B and C are recorded in Table 3 below. They are related to the catalytic activity that is measured for the catalyst A ($A_{HYD1}$).

TABLE 3

Comparison of the Performance Values with Regard to Selective Hydrogenation of a Mixture that Contains Styrene and Isoprene ($A_{HYD1}$) and with Regard to Hydrogenation of Toluene ($A_{HYD2}$).

| Catalyst | Compliant? | Size of the NiO Crystallites (nm) | $A_{HYD1}$ (%) | $A_{HYD2}$ (%) |
|---|---|---|---|---|
| A | Yes | 15.6 | 100 | 100 |
| A' | Yes | 16.2 | 89 | 81 |
| B | No | 14.1 | 49 | 55 |
| C | No | 11.0 | 63 | 42 |

This shows well the enhanced performance values of the catalysts A and A' that are prepared according to the invention and in particular the impact of their specific textural properties. Actually, the catalysts B and C, although having NiO crystallites that are smaller in size than those of the catalysts A and A', have less favorable catalytic performance values. The presence of macropores and mesopores of controlled size is therefore necessary for obtaining the enhanced performance values of the catalysts A and A'.

Example 6: Evaluation of the Catalytic Properties of the Catalysts A, A', B and C with Regard to Hydrogenation of Toluene The catalysts A, A', B and C that are described in the examples above are also tested in relation to the hydrogenation reaction of toluene. The selective hydrogenation reaction is performed in the same autoclave as the one described in Example 5.

Prior to its introduction into the autoclave, a quantity of 2 mL of catalyst is reduced ex situ under a stream of hydrogen from 1 L/h/g of catalyst, at 400° C. for 16 hours (temperature rise slope of 1° C./minute), and then it is transferred into the autoclave, in the absence of air. After adding 216 mL of n-heptane (supplier VWR®, purity>99% HPLC Chromanorm), the autoclave is closed, purged, and then pressurized under 35 bar (3.5 MPa) of hydrogen and brought to the temperature of the test that is equal to 80° C. At time t=0, approximately 26 g of toluene (supplier SDS®, purity>99.8%) is introduced into the autoclave (the initial composition of the reaction mixture is then 6% by weight of toluene/94% by weight of n-heptane), and stirring is begun at 1600 rpm. The pressure is kept constant at 35 bar (3.5 MPa) in the autoclave using a reservoir bottle that is located upstream from the reactor.

The progression of the reaction is followed by taking samples from the reaction medium at regular time intervals: toluene is totally hydrogenated into methylcyclohexane. The consumption of hydrogen is also followed over time by the reduction in pressure in a reservoir bottle located upstream from the reactor. The catalytic activity is expressed in terms of moles of $H_2$ consumed per minute and per gram of Ni.

The catalytic activities that are measured for the catalysts A, A', B and C are recorded in Table 3. They are related to the catalytic activity that is measured for the catalyst A ($A_{HYD2}$). The enhanced performance values of the catalysts A and A' that are prepared according to the invention are shown.

The invention claimed is:

1. Supported catalyst that comprises an oxide substrate that is 90% or more by weight of calcined aluminum with respect to the total weight of the matrix and an active phase that comprises nickel, with the nickel content being between 5 and 65% by weight of said element in relation to the total mass of the catalyst, with said active phase not comprising a metal from group VIB, the nickel particles having a diameter that is less than or equal to 20 nm, said catalyst having a median mesopore diameter of between 8 nm and 25 nm, a median macropore diameter that is greater than 200 nm, a mesopore volume that is measured by mercury porosimetry that is greater than or equal to 0.30 mL/g, and a total pore volume that is measured by mercury porosimetry that is greater than or equal to 0.34 mL/g,
   wherein the catalyst has a macropore volume in the range 20% to 35% of the total pore volume, and
   wherein the catalyst includes NiO crystallites with diameters of 15.6 nm to 16.2 nm.

2. Catalyst according to claim 1, in which the nickel content is between 10 and 34% by weight of said element in relation to the total mass of the catalyst.

3. Catalyst according to claim 1, in which the mesopore volume of the catalyst is between 0.35 mL/g and 0.8 mL/g.

4. Catalyst according to claim 1, which does not contain micropores.

5. Method for preparation of a catalyst according to claim 1, comprising the following steps:
   a) A step for solublization of an acid precursor of aluminum that is selected from among aluminum sulfate, aluminum chloride, and aluminum nitrate in water, at a temperature of between 20 and 90° C., at a pH of between 0.5 and 5, for a period of between 2 and 60 minutes,
   b) A step for adjustment of the pH by adding into the suspension that is obtained in step a) at least one basic precursor that is selected from among sodium aluminate, potassium aluminate, ammonia, sodium hydroxide, and potassium hydroxide, at a temperature of between 20 and 90° C., and at a pH of between 7 and 10, for a period of between 5 and 30 minutes,
   c) A step for co-precipitation of the suspension that is obtained at the end of step b) by adding into the suspension at least one basic precursor that is selected from among sodium aluminate, potassium aluminate, ammonia, sodium hydroxide, and potassium hydroxide, and at least one acid precursor that is selected from among aluminum sulfate, aluminum chloride, aluminum nitrate, sulfuric acid, hydrochloric acid, and nitric acid, at least one of the basic or acid precursors comprising aluminum, with the relative flow rate of the acid and basic precursors being selected in such a way as to obtain a pH of the reaction medium of between 7 and 10, and the flow rate of the acid and basic precursor(s) containing aluminum being regulated in such a way as to obtain a final alumina concentration in the suspension of between 10 and 38 g/L,
   d) A step for filtering the suspension that is obtained at the end of step c) of co-precipitation for obtaining an alumina gel,
   e) A step for drying said alumina gel that is obtained in step d) for obtaining a powder,
   f) A shaping step,
   g) A step of heat treatment that is carried out between steps e) and f) or after step f) at a temperature of between 500 and 1000° C., with or without the presence of an air stream containing up to 60% by volume of water for obtaining a calcined aluminum porous oxide substrate,
   h) A step for impregnating said substrate with a solution that comprises the salt(s) of the precursor(s) of the nickel-based active phase,
   i) A step for drying the impregnated substrate at a temperature of between 15 and less than 250° C., in such a way as to obtain a dried catalyst,
   j) Optionally a heat treatment of said dried catalyst at a temperature of between 250 and 1000° C. with or without the presence of water.

6. Method according to claim 5, in which at least one step k) of reducing treatment is carried out in the presence of a reducing gas after steps i) or j) in such a way as to obtain a catalyst that comprises nickel at least partially in metallic form.

7. Method according to claim 6, in which a step 1) of passivation is carried out by a sulfur-containing compound or an oxidized compound or by $CO_2$ before or after step k) of reducing treatment.

8. Method according to claim 5, in which the concentration of alumina of the alumina gel suspension obtained in step c) is between 13 and 35 g/L.

9. Method according to claim 5, in which the acid precursor of steps a) and c) is selected from among aluminum sulfate, aluminum chloride, and aluminum nitrate, and in which the basic precursor of steps a) and c) is selected from among sodium aluminate and potassium aluminate.

10. Hydrogenation method in which a catalyst prepared according to claim 5 is brought into contact in the presence of hydrogen with a hydrocarbon feedstock that contains polyunsaturated molecules and/or aromatic compounds in such a way as to obtain an at least partially hydrogenated effluent.

11. Hydrogenation method according to claim 10, in which a selective hydrogenation is carried out at a temperature of between 0 and 500° C., at a pressure of between 0.1 and 20 MPa, at a hydrogen/(polyunsaturated compounds to be hydrogenated) molar ratio of between 0.1 and 10, and at an hourly volumetric flow rate of between 0.1 and 200 $h^{-1}$ for a liquid feedstock, between 100 and 15000 $h^{-1}$ for a gaseous feedstock of a hydrocarbon feedstock that contains polyunsaturated compounds that contain at least 2 carbon atoms per molecule and that have a final boiling point that is less than or equal to 250° C.

12. Hydrogenation method according to claim 10, in which hydrogenation of the aromatic compounds is carried out at a temperature of between 30 and 350° C., at a pressure of between 0.1 and 20 MPa, at a hydrogen/(aromatic compounds to be hydrogenated) molar ratio of between 0.1 and 10, and at an hourly volumetric flow rate of between 0.05 and 50 $h^{-1}$ of a hydrocarbon feedstock that contains aromatic compounds and that has a final boiling point that is less than or equal to 650° C.

* * * * *